(12) United States Patent
Faivre et al.

(10) Patent No.: US 8,699,777 B2
(45) Date of Patent: Apr. 15, 2014

(54) METHOD AND APPARATUS FOR COUNTING THROMBOCYTES

(75) Inventors: Magalie Faivre, Grenoble (FR); Patrice Caillat, Grenoble (FR); Myriam-Laure Cubizolles, Grenoble (FR); Christine Peponnet, Seyssinet (FR); Claude Vauchier, St Egreve (FR)

(73) Assignee: Commissariat a l'energie Atomique et aux Energies Alternatives, Paris (FR)

( * ) Notice: Subject to any disclaimer, the term of this patent is extended or adjusted under 35 U.S.C. 154(b) by 872 days.

(21) Appl. No.: 12/769,057

(22) Filed: Apr. 28, 2010

(65) Prior Publication Data

US 2011/0002526 A1  Jan. 6, 2011

(30) Foreign Application Priority Data

Apr. 29, 2009  (FR) .................................... 09 02087

(51) Int. Cl.
*G06K 9/00* (2006.01)
(52) U.S. Cl.
USPC .......................................................... 382/133
(58) Field of Classification Search
USPC .................................................. 382/131–133
See application file for complete search history.

(56) References Cited

U.S. PATENT DOCUMENTS

| | | | | |
|---|---|---|---|---|
| 5,891,734 A * | 4/1999 | Gill et al. | | 436/43 |
| 5,948,752 A * | 9/1999 | Fujita et al. | | 514/13.7 |
| 6,133,995 A | 10/2000 | Kubota | | |
| 6,391,568 B1 | 5/2002 | Schneider et al. | | |
| 6,493,469 B1 * | 12/2002 | Taylor et al. | | 382/284 |
| 6,924,114 B2 | 8/2005 | Wyant et al. | | |
| 7,157,049 B2 * | 1/2007 | Valencia et al. | | 422/68.1 |
| 7,387,880 B2 | 6/2008 | Wyant et al. | | |
| 2002/0160523 A1 | 10/2002 | Wyant et al. | | |
| 2003/0129665 A1 * | 7/2003 | Selvan et al. | | 435/7.2 |
| 2005/0244863 A1 * | 11/2005 | Mir | | 435/6 |
| 2006/0024756 A1 | 2/2006 | Tibbe et al. | | |
| 2009/0203536 A1 * | 8/2009 | Vermette et al. | | 506/9 |
| 2010/0104555 A1 * | 4/2010 | Law et al. | | 424/130.1 |
| 2011/0021696 A1 * | 1/2011 | Kocher et al. | | 524/591 |
| 2011/0027223 A1 * | 2/2011 | Phipps et al. | | 424/85.2 |

FOREIGN PATENT DOCUMENTS

| | | |
|---|---|---|
| WO | WO 02/25280 | 3/2002 |
| WO | WO 2007/068727 | 6/2007 |
| WO | WO 2009/117682 | 9/2009 |

OTHER PUBLICATIONS

Search Report for French Application No. 0902087 dated Jan. 6, 2010.

* cited by examiner

*Primary Examiner* — Elaine Gort
*Assistant Examiner* — Edward Winston, III
(74) *Attorney, Agent, or Firm* — Alston & Bird LLP

(57) ABSTRACT

A method of counting thrombocytes contained in a sample of blood, the method having the steps:
  mixing said sample with:
    fluorescent markers suitable for bonding specifically with the thrombocytes; and
    an agent for inhibiting activation of said thrombocytes;
  introducing the sample (E) into a fluidic chamber (CF) having at least one transparent face;
  acquiring at least one digital image (IN) of said sample by fluorescence microscopy under stationary illumination; and
  counting the thrombocytes (T) present in said or each image by image processing computer means (O).
Apparatus for implementing the method.

15 Claims, 1 Drawing Sheet

METHOD AND APPARATUS FOR COUNTING THROMBOCYTES

FIELD OF THE INVENTION

The invention relates to a method of counting thrombocytes or "platelets" in a sample of blood by specific fluorescent marking and by digital image processing, and it also relates to apparatus for implementing such a method.

BACKGROUND OF THE INVENTION

The method and the apparatus serve in particular to count thrombocytes in a sample of non-lyzed whole blood, that is diluted little or not at all.

Platelets or thrombocytes are blood cells having a diameter of 2 micrometers (μm) to 5 μm without a nucleus and of variable shape. They are present in the blood of a healthy subject at a count of 150,000 to 500,000 per microliter. They are involved in the primary hemostasis process and thus in coagulation. Primary hemostasis serves to stop bleeding due to a capillary lesion, but it needs to be reinforced by coagulation if the damaged blood vessel is of greater caliber. The role of thrombocytes is to clump together after they have been activated and to secrete various substances involved in coagulation such as serotonin, calcium, and adenosine diphosphate that are contained in dense granules of cytoplasm. Platelets thus have a very important role in the coagulation phenomenon. Too great a reduction in the number of platelets gives rise to a risk of hemorrhage (to be envisaged prior to a surgical operation, for example). On the contrary, an increase in their number leads to a risk of thrombosis by forming aggregates of platelets. Platelet disorders may be caused by cirrhosis, renal insufficiency (blood not filtered sufficiently by the kidneys), bone marrow disease, a viral infection, or indeed poisoning (phenylbutazone, phenacetin, acetyl salicylic acid, etc.).

The method commonly used for counting blood cells, in particular thrombocytes, is flow cytometry, even though other alternatives exist, such as centrifuging.

The principle of flow cytometry is to count cells by causing them to travel one by one past a measuring system (optical or electrical). This makes it possible both to count the cells by detecting their passage past the measurement system and also to characterize them (size, conductivity, shape, . . . ). In order to enable the cells to go past one by one, the sample is subjected to very high dilution factors. The two types of flow cytometry are optical cytometry (diffusing light and/or emitting fluorescence) and impedance cytometry. Numerous flow cytometers combine both techniques in order to provide more accurate measurement.

Centrifuging a blood sample in a capillary tube serves to separate the various types of cell depending on their density. The various types of cell are initially marked in specific manner. Red corpuscles go to the bottom of the tube, with plasma on top. Between them there is a zone referred to as the "buffy coat" that contains the platelets and various white corpuscles. A float of appropriate density is used for amplifying the buffy coat so as to improve accuracy. By measuring the thicknesses of the various colored layers, it is possible to deduce the number of particles in each layer and thus the number of each type of cell.

Those methods require relatively large amounts of equipment, consequently they can be implemented only in a specialized laboratory. Furthermore, they require relatively large volumes of blood (at least about 100 microliters (μL)).

A very old method of counting thrombocytes that is practically no longer in use comprises using a hemocytometer. A hemocytometer is a device that is essentially constituted by a fluidic section made using glass with a counting grid etched thereon. A sample of lyzed blood that has been diluted at least 100 times and in which the platelets are marked by a non-specific contrast agent of the Giemsa or Wright dye type is introduced into the hemocytometer, which is then observed in a microscope, thereby enabling cells of interest to be counted manually. That method has been abandoned almost completely because of its poor accuracy and because of the lengthy and difficult work it requires of a specialized operator in order to identify platelets and count them manually.

The article by J. S. Lin et al. "A PC-based imaging system for automated platelet identification", IEEE Transactions on Biomedical Engineering, Vol. 39, No. 9, September 1992, pp. 990-993 describes a method of identifying platelets adhering to a functionalized substrate under flow conditions similar to those encountered in vivo. That method, which includes fluorescent marking of said platelets and using a computer system for processing images, does not make it possible to determine the concentration of platelets in the blood sample, since only cells that adhere to the functionalized substrate are identified.

Documents US 2002/160523 and WO 02/25280 describe methods of detecting thrombocytes based on microvolume laser scanning cytometry ("MLSC"). These methods comprise the introduction of a diluted blood sample into a capillary tube, the scanning of said tube by a focused laser beam and the detection of a fluorescence signal emitted by marked trhombocytes. They are complex and expensive to implement.

SUMMARY OF THE INVENTION

The invention seeks to produce a method that is simple and reliable for counting thrombocytes contained in a sample of blood, and that enables at least some of the drawbacks of the prior art to be overcome.

In accordance with the invention, this object is achieved by a method of counting thrombocytes contained in a sample of blood, the method comprising:
  mixing said sample with:
    fluorescent markers suitable for bonding specifically with the thrombocytes; and
    an agent for inhibiting activation of said thrombocytes;
  introducing the sample into a fluidic chamber having at least one transparent face;
  acquiring at least one digital image of said sample by fluorescence microscopy under stationary illumination; and
  counting the thrombocytes present in said or each image by image processing computer means.

In the framework of the present Application, "microscopy" refers to any technique allowing the observation of microscopic objects, i.e. of objects which are invisible to the unaided eye, in particular with the help of an optical system and of an image detector. "Fluorescence microscopy" refers more specifically to any microscopy technique based on the detection of fluorescence radiation emitted by the objects to be observed.

Illumination is "stationary" when the illuminated region of the sample does not change in a perceptible way during image acquisition. In particular, this excludes any form of scanning of the sample by a focused illumination beam.

In particular implementations of the method of the invention:
  Said step of mixing the blood sample may be implemented prior to injecting the sample into said fluidic chamber.

Conversely, said fluorescent markers and said activation inhibitor agent may be present in the dry state in said fluidic chamber, said mixing step then being performed at the same time as the sample is injected.

Said fluorescent markers may be antibodies, themselves marked with a fluorophore, and suitable for bonding with thrombocytes.

Said thrombocyte activation inhibitor agent may be selected from: prostaglandin E1, dipyridamole, clopidogrel, ticlopidine, and acetyl salicylic acid.

Provision may also be made for mixing the sample of blood with an anticoagulant.

The sample of blood need not be diluted, other than by adding the reagents needed for detection purposes (anticoagulants, markers, activation inhibitor agent). In a variant, the sample may be diluted by a factor that is less than or equal to 50.

Said fluidic chamber may present thickness lying in the range 15 μm to 60 μm.

The step of acquiring at least one digital image of said sample may be performed by epifluorescence microscopy and/or by an imaging device comprising a CDD or CMOS matrix detector.

The step of counting thrombocytes may include a step of thresholding and binarizing the pixels of the or each image, followed by an operation of counting proper.

The volume of said sample of blood, prior to said mixing step, may lie in the range 1 μL to 100 μL.

Said sample of blood may be a sample of non-lyzed whole blood.

A step that consists in deducing a number of thrombocytes per unit volume in the sample of blood from the number of thrombocytes identified in said or each digital image may be provided.

Preferably, said fluidic chamber does not comprise any functionalized surface.

Preferably, the sample does not flow inside said fluidic chamber.

The invention also provides apparatus for counting thrombocytes, the apparatus comprising:
  a fluidic chamber into which a sample of blood can be introduced, the chamber having a wall that is at least partially transparent and containing: an agent for inhibiting activation of said thrombocytes; and fluorescent markers suitable for bonding specifically with said thrombocytes;
  a source of light for performing stationary illumination of said sample in such a way as to excite said fluorescent markers;
  a fluorescence microscopy optical system for acquiring at least one digital image of the fluorescence of said sample; and
  computer means for image processing adapted to count the thrombocytes present in said or each fluorescence image in automatic manner.

BRIEF DESCRIPTION OF THE DRAWINGS

Other characteristics, details, and advantages of the invention appear on reading the description made with reference to the accompanying drawing, given by way of example and in which.

DETAILED DESCRIPTION

The principle of the method relies on computer acquisition and analysis of images themselves acquired by microscope, of a sample of blood in which the thrombocytes have been inactivated and marked in a special manner.

By way of example, there follows an explanation of a protocol implementing such a method.

A sample of whole blood is taken on an anticoagulant such as ethylene-diamine-tetraacetic (EDTA) acid deposited dry at a concentration of 1.8 milligrams per milliliter (mg/mL), or liquid sodium citrate at a concentration of 1 volume for 9 volumes of blood. Thereafter, a volume of 5 μL of the sample is mixed with 45 μL of saline buffer (phosphate buffer saline (PBS)), thereby diluting it ten times. Dilution is not essential for implementation, but it makes it easier to count thrombocytes by image analysis by increasing their mean separation and thus avoiding overlapping effects that could lead to an under-estimation of the actual number of cells.

A volume of 0.5 μL of phostaglandin E1 is added to inactivate the thrombocytes and thus prevent them from aggregating.

Thereafter, 10 μL of marked antibody (anti-CD61 FITC at 0.5 mg/mL) are added to the solution to mark the thrombocytes in a specific manner. Anti-CD61 is an antibody suitable for bonding with thrombocytes, and FITC (fluorescein iso thio cyanate) is a commonly used fluorophore.

The mixture is homogenized by being successively sucked and expelled in and out of a micropipette μP; thereafter it is left to incubate at ambient temperature, in the dark, for 15 minutes.

It is of interest to observe that the use of an anticoagulant is not essential if incubation time is limited to about 3 to 5 minutes, which seems to be sufficient for achieving marking. In contrast, adding prostaglandin E1 or some other inhibitor of thrombocyte activation has been found to be essential. In its absence, the thrombocytes become active and even in the presence of an anticoagulant they form aggregates, thereby preventing them from being counted.

After incubation, the sample E obtained by mixing blood with the diluant and the various reactions (anticoagulant, anti-activator, marked antibody) is inserted into a fluidic chamber CF having at least one transparent face, which chamber may be constituted by two glass microscope slides L1 and L2 held together by two adhesive strips BA so as to define a fluidic section with a thickness of the order of 30 μm. Filling may be performed very simply by capillarity.

Figure 1:
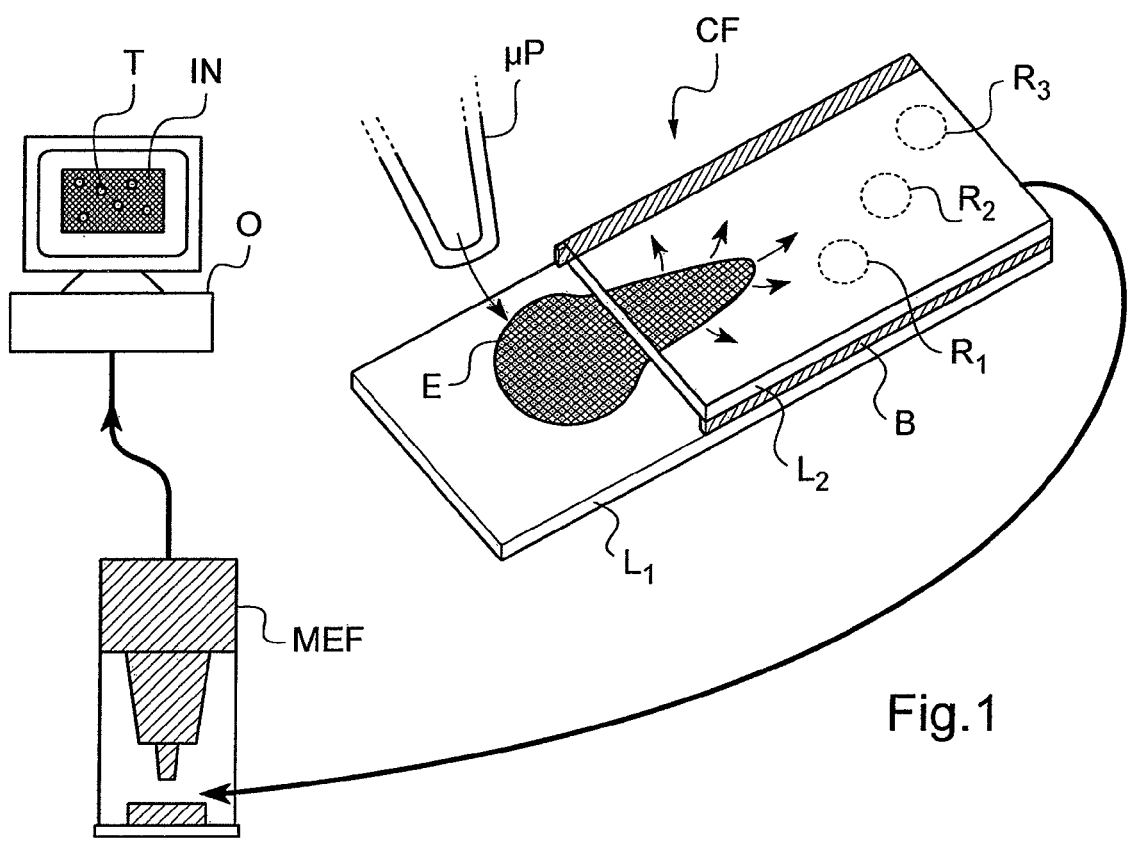
FIG. 1 shows the principle of the method.

Thereafter, the fluidic chamber, or rather a region of said chamber, is observed in an epifluorescence microscope MEF of conventional type having a source of light for exciting fluorophores and an optical system for acquiring fluorescence images, which system is connected to a computer O. It is possible to perform a plurality of observations at a plurality of different locations in the chamber (e.g. the three regions R1, R2, and R3 in FIG. 1) in order to compensate for any residual non-uniformities.

While the sample is kept, without flowing, within the chamber, one or more digital images IN are acquired in which the marked thrombocytes appear as dots or points of light T that are isolated because of the anti-activation agent that prevents them from aggregating, against a darker background. Thereafter, the image(s) is/are processed by a computer as follows:
  contrast is increased, and brightness is adjusted by the user;
  a binarization threshold is defined so as to convert the images from a gray scale format to a binary black-and-white format; and
  the number of objects (white points, or black points if working in negative) is counted directly in automatic manner.

Assuming that each object in the image represents one and only one thrombocyte, this determines a number of cells in each observation window. The mean of the values as determined in this way is then converted into a number of cells per unit volume by estimating the volume of the fluidic chamber that corresponds to an observation window of the microscope.

The entire measurement takes about 20 minutes, from taking the blood sample to obtaining the platelet count. This time may be further reduced by shortening the incubation period.

The method of the invention is compared with counting thrombocytes by flow cytometry using an analyzer combining optical measurement and electrical measurement, the analyzer being an automated "Coulter LH 780 Hematology Analyzer".

The reference measurements in flow cytometry were performed on samples of 200 µL of total blood taken on EDTA and diluted by a factor of 6250. For the method of the invention, the above-described protocol was applied. It should be observed that the invention makes it possible to make use of quantities of blood that are much smaller than those required for flow cytometry.

Figure 2:
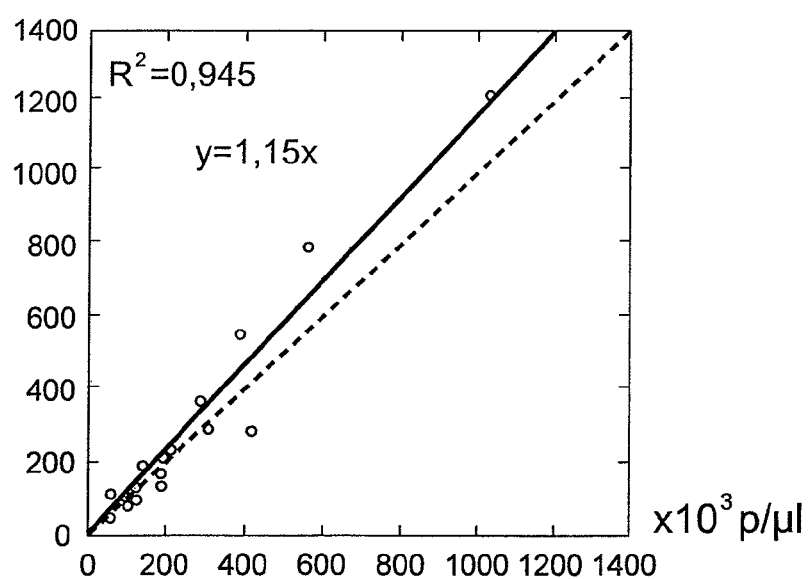
FIG. 2 is a graph illustrating its performance.

FIG. 2 serves to compare the platelet count values obtained by the reference method (abscissa axis x) and by the method of the invention (ordinate axis y) for 17 samples of total blood from different patients.

The correlation is linear: y=1.15x with a good linear regression coefficient ($R^2$=0.945); the repeatability of the measurement is satisfactory (the coefficient of variation (CV), representing the standard deviation of the measurement divided by the average and expressed as a percentage, being less than or equal to 10% for a platelet concentration lying in the range 50,000 $\mu L^{-1}$ to 1,000,000 $\mu L^{-1}$). By way of comparison, the variation in the reference method given by the CV lies in the range 3.3% to 6.6%, depending on the ranges of platelet concentration (3.3% in the range 280,000 $\mu L^{-1}$ to 320,000 $\mu L^{-1}$ and 6.6% in the range 90,000 $\mu l^{-1}$ to 110,000 $\mu L^{-1}$). These results could be improved by using fluidic chambers of more uniform thicknesses.

The hematocrit of the analyzed samples lay in the range 25% to 46%; it was verified that this variation in the hematocrit ratio has no significant influence on the results obtained.

The method of the invention is described above with reference to a particular implementation; however numerous modifications may be envisaged. In particular:

Any known anticoagulant may be used instead of or in addition to EDTA, e.g. sodium citrate or heparin.

As mentioned above, diluting the sample is not essential, however it enables image processing to be used that is particularly simple by reducing the probability of two or more platelets overlapping on the image. If it is desired to work without dilution, it is necessary to provide image processing that is more complex, serving to measure the areas of recorded fluorescent objects in order to determine whether they correspond to one or more platelets.

The dilution ratio should not be too great so as to avoid degrading counting statistics, given that the method of the invention provides for observation of very small volumes of blood. Typically, dilution ratios lying in the range 0 (no dilution) to 50, and preferably equal to about 10, are found to be appropriate for implementing the invention.

The diluant may be PBS, a solution of thyorode mixed with 4-(2-hydroxyethyl)piperazine-1-ethanesulfonic acid, trishydroxymethyl-aminomethane, or any other saline buffer that maintains the osmolarity of the sample and the pH at physiological values.

The anti-activator may be prostaglandin E1, dipyridamole, clopidogrel, ticlopidine, acetyl salicylic acid (or aspirin). Any other agent for preventing platelets from clumping may be used, e.g. acting by:
  increasing the quantity of cyclic nucleotides;
  inhibiting arachidonic acid metabolism;
  inhibiting membrane receivers;
  inhibiting activation processes (inhibiting calcium channels, inhibiting calmodulin, inhibiting the cytoskeleton, . . . ); and
  inhibiting the formation and/or the action of thrombin.

The marking antibody may be selected so as to maximize its affinity with the cells of interest. For this purpose, the clone having the greatest affinity should be selected.

As described above, the incubation time should advantageously be as short as possible, while ensuring that practically all of the platelets are marked. If the incubation time is short enough, it may be found that using an anticoagulant is superfluous.

The fluorophore coupled to the antibody may be different, for example fluorescein iso thio cyanate (FITC), peridinin chlorophylle protein (PerCP), R-phycoerhtyrin (or R-PE), etc.

The thickness of the fluidic section may lie in the range 15 µm to 60 µm. A smaller thickness could lead to problems of filling since the height of the chamber would then be of the same order of magnitude as the size of the largest blood cells. Too great a thickness would lead to a risk of platelets overlapping in the image, and as a result, would require an optical system to be used having excessive resolution in order to be capable of visualizing platelets in the thickness of the section.

In the implementation described in detail, the fluidic chamber is constituted by two superposed glass slides united by strips of adhesive. Preferably, said glass slides are not functionalized. In fact, the aim of the invention is not to determine the number of platelets having adhered to a limited surface, but to count the overall number of platelet contained in the sample.

Naturally, any other appropriate microfluidic device could be used. In particular, the fluidic chamber could be incorporated in a microfluidic chip. It is necessary that at least some zones of the top face thereof are transparent at the excitation and emission wavelength of the fluorophores in order to enable the marked platelets to be observed. Biocompatible materials other than glass could be used, such as polycarbonate.

Fluorescence imaging techniques other than epifluorescence microscopy could be used.

Provision may also be made to regulate the temperature of the sample.

When the dilution rate is small, e.g. less than 5, or when there is no dilution (dilution rate equal to 0), the assumption that each point of light in the fluorescence image corresponds to one and only one thrombocyte may lead to an underestimate in determining the number of thrombocytes. Since the thrombocytes are more concentrated, the fluorescence signals may overlap. This under-estimation may be attenuated by using more refined image processing that takes account of the shape and/or the area of each detected point.

A device according to the invention comprises an excitation light source. According to a preferred embodiment, said light source is adapted for illuminating in a stationary way (and therefore without scanning) a significant portion of the sample surface. In the framework of the present Application, "a significant portion" means at least 10% of the surface, preferably at least 20% or 30%, or even 100%. This excitation light source is not focused. It can be an incandescence lamp of a LED. Preferably, a wavelength filter is placed between the light source and the sample to ensure that the light reaching the sample has a wavelength corresponding to the excitation wavelength of the fluorescent marker.

The light source can be placed at a distance from the sample comprised e.g. between 1 mm and 1 cm. It is preferably static, i.e. fixed in front of the sample. It emits a light cone centered on a fixed axis. In fact, as discussed above, in the method of the invention the radiation emitted by the source is not required to perform a scan. This reduces the cost and the complexity of the implementation.

Preferably, the detector comprises and image detector, i.e. a pixelized matrix detector whose field of view covers a significant portion of the sample, or even the whole sample. This detector allows obtaining a fluorescence image of the observed field in a very short time (between a few hundreds of milliseconds and a few seconds). It can be e.g. a detector comprising an object lens connected with a CCD or a CMOS matrix. The detector can be placed on the same side of the source relative to the sample (operation in reflection) or on the opposite side (operation in transmission).

Thus, a device according to the invention preferably comprises a fixed and non-collimated light source, a matrix image detector and a microfluidic chamber. It is a cheap, portable and simple device, which does not require any movement of the source and/or detector relative to the sample.

The invention claimed is:

1. A method of counting thrombocytes contained in a sample of blood, the method comprising:
    mixing said sample with:
        fluorescent markers suitable for bonding specifically with the thrombocytes; and
        an agent for inhibiting activation of said thrombocytes;
    introducing the sample into a fluidic chamber having at least one transparent face;
    acquiring at least one digital image of said sample by fluorescence microscopy under stationary illumination; and
    counting the thrombocytes present in said or each image by image processing computer means
    wherein said fluorescent markers and said activation inhibitor agent are present in a dry state in said fluidic chamber, whereby said mixing step is performed while the sample is injected.

2. A method of counting thrombocytes according to claim 1, wherein said fluorescent markers are antibodies, themselves marked with a fluorophore, and suitable for bonding with thrombocytes.

3. A method of counting thrombocytes according to claim 1, wherein said thrombocyte activation inhibitor agent is selected from: prostaglandin E1, dipyridamole, clopidogrel, ticlopidine, and acetyl salicylic acid.

4. A method of counting thrombocytes according claim 1, further comprising the step of mixing the sample of blood with an anticoagulant.

5. A method of counting thrombocytes according to claim 1, wherein the sample of blood is not diluted.

6. A method of counting thrombocytes according to claim 1, further comprising the step of diluting the sample of blood by a factor less than or equal to 50.

7. A method of counting thrombocytes according to claim 1, wherein said fluidic chamber presents thickness lying in the range 15 μm to 60 μm.

8. A method of counting thrombocytes according to claim 1, wherein the step of acquiring at least one digital image of said sample is performed by epifluorescence microscopy.

9. A method of counting thrombocytes according to claim 1, wherein the step of counting thrombocytes includes a step of thresholding and binarizing the pixels of the or each image, followed by an operation of counting proper.

10. A method of counting thrombocytes according claim 1, wherein the volume of said sample of blood, prior to said mixing step, lies in the range 1 μL to 100 μL.

11. A method of counting thrombocytes according claim 1, wherein said sample of blood is a sample of non-lyzed whole blood.

12. A method of counting thrombocytes according to claim 1, also including a step that comprises in deducing a number of thrombocytes per unit volume in the sample of blood from the number of thrombocytes identified in said or each digital image.

13. A method of counting thrombocytes according to claim 1, wherein said fluidic chamber does not comprise any functionalized surface.

14. A method of counting thrombocytes according claim 1, wherein the sample does not flow inside said fluidic chamber.

15. Apparatus for counting thrombocytes, the apparatus comprising:
    a fluidic chamber into which a sample of blood can be introduced, the chamber having a wall that is at least partially transparent and containing: an agent for inhibiting activation of said thrombocytes; and fluorescent markers suitable for bonding specifically with said thrombocytes;
    a source of light for performing stationary illumination of said sample in such a way as to excite said fluorescent markers;
    a fluorescence microscopy optical system for acquiring at least one digital image of the fluorescence of said sample; and
    computer means for image processing adapted to count the thrombocytes present in said or each fluorescence image in automatic manner,
    said agent for inhibiting activation of said thrombocytes and said fluorescent markers suitable for bonding specifically with said thrombocytes being in a dry state in said fluidic chamber.

* * * * *